United States Patent [19]

Nestler et al.

[11] Patent Number: 5,093,520
[45] Date of Patent: Mar. 3, 1992

[54] PREPARATION OF MONOETHYLENICALLY UNSATURATED CARBOXYLATES

[75] Inventors: Gerhard Nestler, Ludwigshafen; Peter Ruckh, Mannheim; Manfred Lazarus, Nussloch, all of Fed. Rep. of Germany

[73] Assignee: BASF Aktiengesellschaft, Ludwigshafen, Fed. Rep. of Germany

[21] Appl. No.: 718,644

[22] Filed: Jun. 21, 1991

[30] Foreign Application Priority Data

Jun. 21, 1990 [DE] Fed. Rep. of Germany ....... 4019781

[51] Int. Cl.$^5$ .............................................. C07C 67/48
[52] U.S. Cl. ................................................... 560/218
[58] Field of Search ........................................ 560/218

[56] References Cited

FOREIGN PATENT DOCUMENTS 299743   1/1989  European Pat. Off.
45-01443 1/1970  Japan
2042948  2/1987  Japan
2123150  6/1987  Japan
2-017150 1/1990  Japan

OTHER PUBLICATIONS

Ullmann's Encyclopedia of Industrial Chemistry, vol. A1, 1985, pp. 168–169.

*Primary Examiner*—Paul J. Killos
*Attorney, Agent, or Firm*—Oblon, Spivak, McClelland, Maier & Neustadt

[57] ABSTRACT

Monoethylenically unsaturated carboxylates are prepared by a process in which, following esterification, a) the product mixture is extracted in a first extraction stage with from 5 to 30% v/v of water, based on the product mixture, at a temperature of from 10° to 40° C., and b) the aqueous phase from the first extraction stage is extracted, in a second extraction stage, with from one to four times its weight of the alkanol to be esterified, at a temperature of from 10° to 30° C.

1 Claim, No Drawings

PREPARATION OF MONOETHYLENICALLY UNSATURATED CARBOXYLATES

The present invention relates to a process for the preparation of a monoethylenically unsaturated carboxylate, in which an $\alpha,\beta$-ethylenically unsaturated carboxylic acid having from 3 to 5 carbon atoms is esterified with a $C_6$–$C_{14}$-alkanol in a molar ratio of from 0.8:1 to 1.2:1 in the liquid phase at a temperature of from 85° to 140° C. in the presence of an effective amount of a polymerization inhibitor and an inert entraining agent for water and in the presence of from 0.1 to 5% w/w of sulfuric acid, based on the carboxylic acid/alkanol mixture, whereafter the product mixture resulting from said esterification is separated into aqueous and organic phases by extraction and the monoethylenically unsaturated carboxylate formed is isolated from the organic phase.

Monoethylenically unsaturated carboxylates from $\alpha,\beta$-ethylenically unsaturated carboxylates having from 3 to 5 carbon atoms and alkanols having from 6 to 14 carbon atoms have, among other applications, significance as monomers for the preparation of polymers for use, for example, in aqueous polymer dispersions effective as adhesives.

*Ullmann's Encyclopedia of Industrial Chemistry*, Vol. A1, pp. 168-169, 1985, VCH, Weinheim, GFR, describes a process for the preparation of esters from higher alkanols and acrylic acid in a molar ratio of from 1:1 to 1.1:1 at a temperature of from 85° to 95° C. in liquid phase in the presence of a polymerization inhibitor and sulfuric acid and an entraining agent for water, which process is characterized in that the product mixture obtained after the esterification step is extracted with aqueous alkali solution to give an organic phase from which the acrylate is isolated. A drawback of this process is that the alkylsulfuric acid which is formed from the sulfuric acid and alkanol parallel to the esterification reaction (and which in fact constitutes the catalytically active acid) and any sulfuric acid not esterified with alkanol are converted during the extraction stage to corresponding alkali metal salts which are of no value and are not, as such, capable of being re-used for further esterification. This is particularly undesirable under conditions of continuous operation, where it leads to continual loss of valuable educt. For a similar reason, this prior process would not be suitable for modification so as to effect esterification in the presence of an excess of acrylic acid, since unconverted acrylic acid would be converted to its alkali metal salt during extraction. In typical equilibrium reactions such as esterification reactions, an excess of one starting component over the other causes an increase in the degree of conversion of the latter.

It is an object of the invention, therefore, to provide a process, less subject to the above drawbacks, for the preparation of a monoethylenically unsaturated carboxylate, in which an $\alpha,\beta$-ethylenically unsaturated carboxylic acid is esterified with a higher alkanol in the liquid phase at elevated temperature in the presence of a polymerization inhibitor and an inert entraining agent for water and also in the presence of sulfuric acid, whereafter the product mixture resulting from said esterification is separated into aqueous and organic phases by extraction and the monoethylenically unsaturated carboxylate formed is isolated from the organic phase.

Accordingly, we have found a novel process for the preparation of a monoethylenically unsaturated carboxylate, in which an $\alpha,\beta$-ethylenically unsaturated carboxylic acid having from 3 to 5 carbon atoms is esterified with a $C_6$–$C_{14}$-alkanol in a molar ratio of from 0.8:1 to 1.2:1 in the liquid phase at a temperature of from 85° to 140° C. in the presence of an effective amount of a polymerization inhibitor and an inert entraining agent for water and also in the presence of from 0.1 to 5% w/w of sulfuric acid, based on the carboxylic acid/alkanol mixture, whereafter the product mixture resulting from said esterification is separated into aqueous and organic phases by extraction and the monoethylenically unsaturated carboxylate formed is isolated from the organic phase, wherein, on completion of the esterification, a) the product mixture is extracted in a first extraction stage with from 5 to 30% v/v of water, based on the product mixture, at a temperature of from 10° to 40° C., and b) the aqueous phase from the first extraction stage is extracted, in a second extraction stage, with from one to four times its weight of the alkanol to be esterified, at a temperature of from 10° to 30° C.

The extraction of the product mixture with water may be carried out in a single operation or in a number of stages following the mixer-settler principle or some other well-known method of extraction as described, for example, in *Ullmanns Encyclopadie der technischen Chemie*, Vol. 2, pp. 560–564, 1972, VCH, 6940 Weinheim, GFR. During extraction, the acids contained in the product mixture are taken up by the aqueous phase, the efficiency of extraction with respect to alkylsulfuric acid plus sulfuric acid usually being from 90 to 99%, whereas with respect to any unconverted monoethylenically unsaturated carboxylate it is generally from 50 to 90%. The extraction temperature in the first extraction stage is preferably adjusted by cooling the product mixture to a temperature of from 10° to 60° C. and extracting it with water having a temperature of from 10° to 30° C., which normally results in a mixture temperature of from 10° to 40° C.

In the extraction of the acid-containing aqueous phase from the first extraction stage, the amount of acids transferred to the alkanolic phase is usually such as to give a final total content of alkylsulfuric acid and sulfuric acid in the alkanolic phase of from 80 to 95% molar based on the amount of sulfuric acid originally used for the esterification, whereas this value for the $\alpha,\beta$-monoethylenically unsaturated carboxylates is from 40 to 80% molar based on the amount, if any, of $\alpha,\beta$-monoethylenically unsaturated carboxylates remaining unconverted after the esterification reaction.

Surprisingly, no appreciable side-reactions occur in the process of the invention either in the first or in the second extraction stage. For instance, neither saponification of the ester nor addition of water to the double bond has been observed in the first extraction stage. This is all the more remarkable due to the fact that the extraction medium is distinctly acidic, on account of the relatively small amount of water used for extraction, and the treatment of unsaturated carboxylates with aqueous solutions of strong acids normally causes both acid-catalyzed splitting of the ester and acid-catalyzed addition of water to the double bond.

Similarly, both the acid-catalyzed formation of dialkyl ethers and the acid-catalyzed formation of dialkyl sulfates would have been expected in the second extraction stage. Therefore, the alkanolic phase from the second extraction stage, which contains essentially the sulfuric acids having a catalytic effect on the actual esterification reaction plus any unconverted α,β-monoethylenically unsaturated carboxylic acid, can be advantageously recycled to the esterification stage, and the aqueous phase from the second extraction stage, which contains essentially water only, is advantageously suitable for re-use in the first extraction stage after replenishment, if necessary, by a small amount of fresh water. This procedure is particularly advantageous when the process is carried out continuously. However, the process of the invention may, of course, be operated batchwise. When a continuous procedure is adopted, the amount of alkanol used for extraction in the second extraction stage of the process of the invention is such as not to exceed the amount of alkanol required for esterification in the esterification stage. Again, when the process of the invention is carried out continuously, the organic phase coming from the first extraction stage is conveniently fractionated to give the monoethylenically unsaturated carboxylate formed, any unconverted alkanol, the entraining agent, and bottoms, of which the entraining agent and unconverted alkanol, if any, are advantageously recycled to the esterification stage. If distillates of particularly high purity are desired, it is recommended that the organic phase be neutralized with a dilute aqueous alkali metal hydroxide solution. The bottoms normally contain the polymerization inhibitor, which is usually readily soluble in organic liquids. Examples of suitable polymerization inhibitors are hydroquinone, 4-methoxyphenol, and phenothiazine, which may be used singly or in admixture with each other. It is usual to add from about 0.01 to 0.1% w/w of polymerization inhibitor to the esterification mixture and mixtures containing the unsaturated ester. The said bottoms may be used for this purpose, if convenient. A particularly suitable entraining agent for water is cyclohexane. Alternatively, agents such as chlorinated hydrocarbons or tuluene may be used to the same end. The essential advantage of the process of the invention resides in its increased economic value. This advantage assumes particular importance when acrylic or methacrylic acid is to be esterified with alkanols having from 6 to 10 carbon atoms, preferably 2-ethylhexanol, and especially when the acid to be esterified is employed in excess.

EXAMPLE 1

A mixture of 360 g of acrylic acid, 790 g of n-decanol, 200 g of cyclohexane, 10 g of 97% sulfuric acid, 0.4 g of phenothiazine, and 0.4 g of 4-methoxyphenyl was heated to the boil for 3 hours, and the water of reaction was removed azeotropically. The product mixture thus obtained contained 10.2 g of acrylic acid and 23.4 g of decylsulfuric acid. The degree of conversion of the n-decanol used was 99.1%. The product mixture, which weighed 1270 g, was then extracted twice at 40° C. with 150 g of water each time following the mixer-settler principle, and the resulting aqueous phase was treated twice in a similar manner with 300 g of n-decanol each time. The combined decanol phases (636 g) contained 5.6 g of acrylic acid and 21.2 g of decylsulfuric acid. The organic phase from the first extraction stage contained, as determined by gas chromatography, 96% of theory of desired ester of acrylic acid and n-decanol, based on the amount of n-decanol used.

EXAMPLE 2 a) A mixture of 360 g of acrylic acid, 650 g of 2-ethylhexanol, 200 g of cyclohexane, 5 g of 97% sulfuric acid, 0.4 g of phenothiazine, and 0.4 g of 4-methoxyphenyl was heated to the boil for 3 hours, and the water of reaction was removed azeotropically. The product mixture thus obtained contained 8.7 g of acrylic acid and 10.4 g of 2-ethylhexylsulfuric acid. The degree of conversion of the 2-ethylhexanol used was 98.7%. The product mixture, which weighed 1110 g, was then extracted at 30° C. with 150 g of water following the mixer-settler principle, and the resulting aqueous phase was treated twice in a similar manner with 225 g of 2-ethylhexanol each time. The combined 2-ethylhexanol phases (475 g) contained 3.9 g of acrylic acid and 9.5 g of 2-ethylhexylsulfuric acid. The organic phase from the first extraction stage contained, as determined by gas chromatography, 97% of theory of the target ester of acrylic acid and 2-ethylhexanol, based on the amount of 2-ethylhexanol used.

b) The procedure described in a) was repeated except that the 2-ethylhexanol used was the 2-ethylhexanol phase from the second extraction stage of a) together with 195 g of fresh 2-ethylhexanol. Also, in place of 5 g of sulfuric acid there were added only 2 g of sulfuric acid, and the first extraction of the product mixture was effected with the aqueous phase from the second extraction stage of a) replenished with 10 g of water. The product mixture thus obtained contained 14 g of acrylic acid and 13.2 g of 2-ethylhexylsulfuric acid. The combined 2-ethylhexanol phases from the second extraction contained 7.7 g of acrylic acid and 12.1 g of 2-ethylhexylsulfuric acid. The yield of target ester was 98.2% of theory, based on the amount of 2-ethylhexanol used.

EXAMPLE 3 a) A mixture of 435 g of methacrylic acid, 650 g of 2-ethylhexanol, 200 g of cyclohexane, 5.6 g of 97% sulfuric acid, 0.4 g of phenothiazine, and 0.4 g of 4-methoxyphenyl was heated to the boil for 4 hours, and the water of reaction was removed azeotropically. The product mixture thus obtained contained 17.8 g of methacrylic acid and 11.5 g of 2-ethylhexylsulfuric acid. The degree of conversion of the 2-ethylhexanol used was 98.2%. The product mixture, which weighed 1196 g, was then extracted twice at 30° C. with 100 g of water following the mixer-settler principle, and the resulting aqueous phase was treated twice in a similar manner with 200 g of 2-ethylhexanol each time. The combined 2-ethylhexanol phases (419 g) contained 7.3 g of methacrylic acid and 10.5 g of 2-ethylhexylsulfuric acid. The organic phase from the first extraction stage contained, as determined by gas chromatography, 96.8% of target ester of methacrylic acid and 2-ethylhexanol, based on the amount of 2-ethylhexanol used.

b) The procedure described in a) was repeated except that the 2-ethylhexanol used was the 2-ethylhexanol phase from the second extraction stage of a) together with 273 g of fresh 2-ethylhexanol. Also, in place of 5 g of sulfuric acid there were added only 2 g of sulfuric acid, and the first extraction of the product mixture was effected with the aqueous phase from the second extraction stage of a) replenished with 10 g of water. The product mixture thus obtained contained 12.9 g of methacrylic acid and 14.4 g of 2-ethylhexylsulfuric acid. The degree of conversion of the 2-ethylhexanol used was 98.3%. The combined 2-ethylhexanol phases from the second extraction contained 6.2 g of methacrylic acid and 13.3 g of 2-ethylhexylsulfuric acid. The yield of target ester was 97.9% of theory, based on the amount of 2-ethylhexanol used.

We claim:

1. A process for the preparation of a monoethylenically unsaturated carboxylate, in which an $\alpha,\beta$-ethylenically unsaturated carboxylic acid having from 3 to 5 carbon atoms is esterified with a $C_6$–$C_{14}$-alkanol in a molar ratio of from 0.8:1 to 1.2:1 in the liquid phase at a temperature of from 85° to 140° C. in the presence of an effective amount of a polymerization inhibitor and an inert entraining agent for water and also in the presence of from 0.1 to 5% w/w of sulfuric acid, based on the carboxylic acid/alkanol mixture, whereafter the product mixture resulting from said esterification is separated into aqueous and organic phases by extraction and the monoethylenically unsaturated carboxylate formed is isolated from the organic phase, wherein, on completion of the esterification, a) the product mixture is extracted in a first extraction stage with from 5 to 30% v/v of water, based on the product mixture, at a temperature of from 10° to 40° C., and b) the aqueous phase from the first extraction stage is extracted, in a second extraction stage, with from one to four times its weight of the alkanol to be esterified, at a temperature of from 10° to 30° C.

* * * * *